United States Patent [19]
Joshi et al.

[11] Patent Number: 6,045,055
[45] Date of Patent: Apr. 4, 2000

[54] DEVICE AND METHOD FOR DELIVERING FLUID

[75] Inventors: Ashok V. Joshi, Salt Lake City; John Joseph McEvoy, Sandy; Truman Christian Wold, II, Salt Lake City, all of Utah

[73] Assignee: Ceramatec, Inc., Salt Lake City, Utah

[21] Appl. No.: 09/065,923

[22] Filed: Apr. 24, 1998

Related U.S. Application Data

[63] Continuation-in-part of application No. 08/804,286, Mar. 3, 1997, abandoned.

[51] Int. Cl.⁷ .................................................. A61L 9/12
[52] U.S. Cl. ......................................... 239/6; 239/45
[58] Field of Search ............................. 239/34, 44, 6, 239/45, 289; 422/124, 122; 261/119.1

[56] References Cited

U.S. PATENT DOCUMENTS

| | | |
|---|---|---|
| 1,567,957 | 12/1925 | Kesselman . |
| 3,877,152 | 4/1975 | Gorman . |
| 4,166,087 | 8/1979 | Cline et al. .................. 261/119.1 |
| 4,654,198 | 3/1987 | Berardini ......................... 422/124 |
| 4,919,981 | 4/1990 | Levey et al. . |
| 5,029,729 | 7/1991 | Madsen et al. ..................... 222/1 |
| 5,068,099 | 11/1991 | Sramek . |
| 5,077,102 | 12/1991 | Chong . |
| 5,196,171 | 3/1993 | Peltier . |
| 5,373,581 | 12/1994 | Smith . |
| 5,431,859 | 7/1995 | Tobin . |
| 5,589,132 | 12/1996 | Zippel ................................ 422/24 |
| 5,704,832 | 1/1998 | Borrell ............................. 422/124 |

*Primary Examiner*—Kevin Weldon
*Attorney, Agent, or Firm*—Factor and Shaftal

[57] ABSTRACT

The present invention is directed to a device for delivering a fluid to the surrounding environment. The device includes a housing having an interior region and at least one opening, a fluid contained within the interior region, and a device means to force the fluid through the opening, and against gravity. Such a forcing device preferably comprises a gas generating pump, designed to force fluid positioned below the opening through a channel or conduit and out of the housing. Moreover, the opening in the housing may be associated with a member for controllably releasing fluid from the housing, for instance one or more porous plugs, an emanator pad, a decorative element or an adjustable valve. Additionally, the invention contemplates the use of a moveable member, such as a piston, flexible bladder, or expandable bladder, to separate the fluid from the gas generating pump and assist is forcing fluid out of the housing.

20 Claims, 3 Drawing Sheets

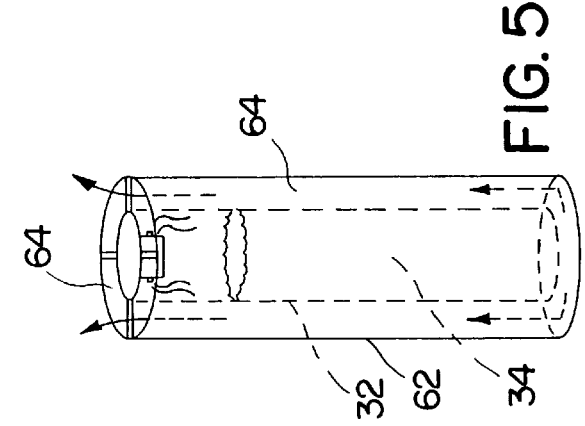
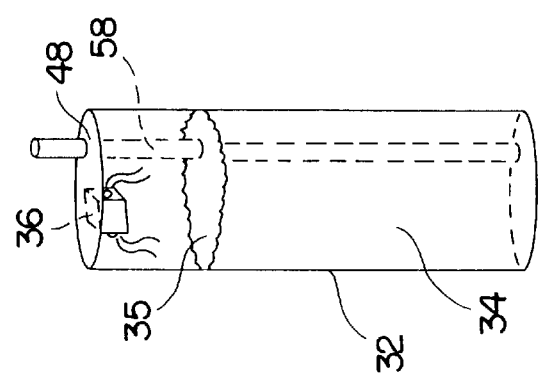
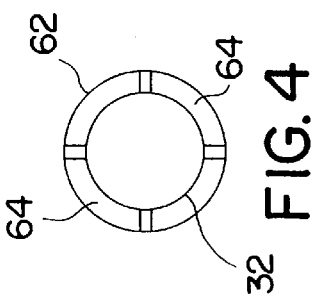
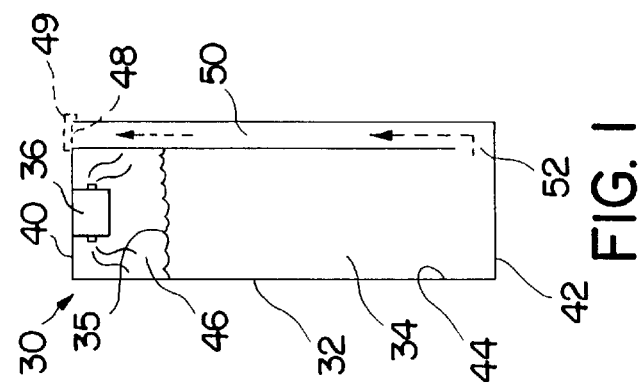
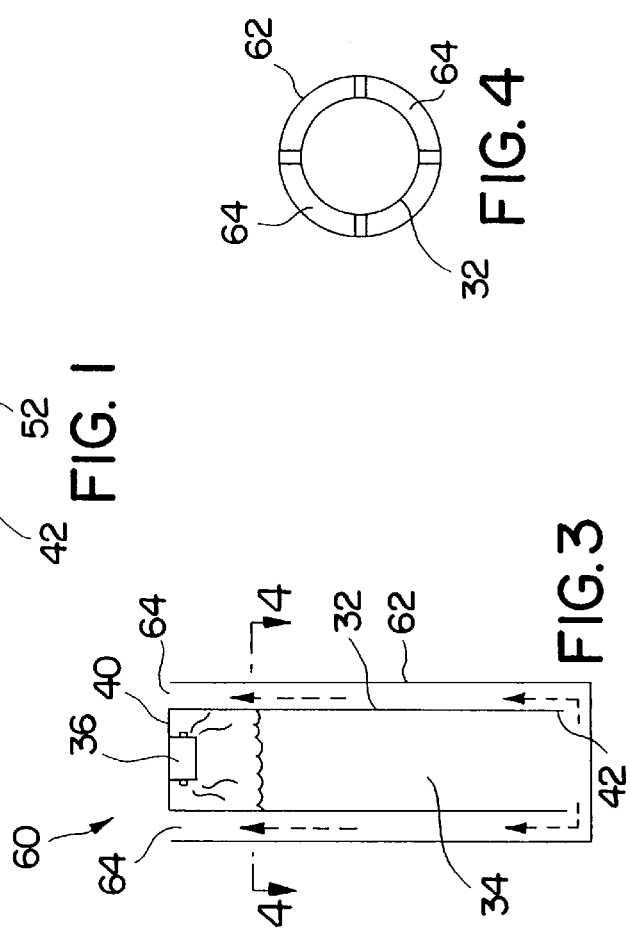

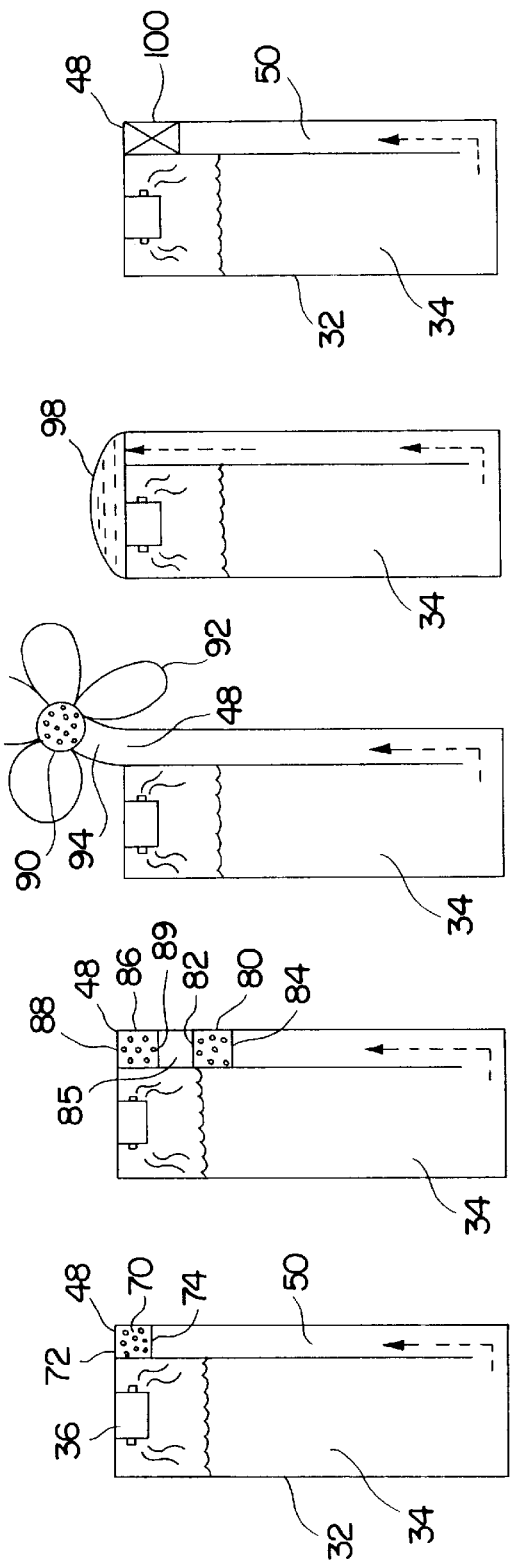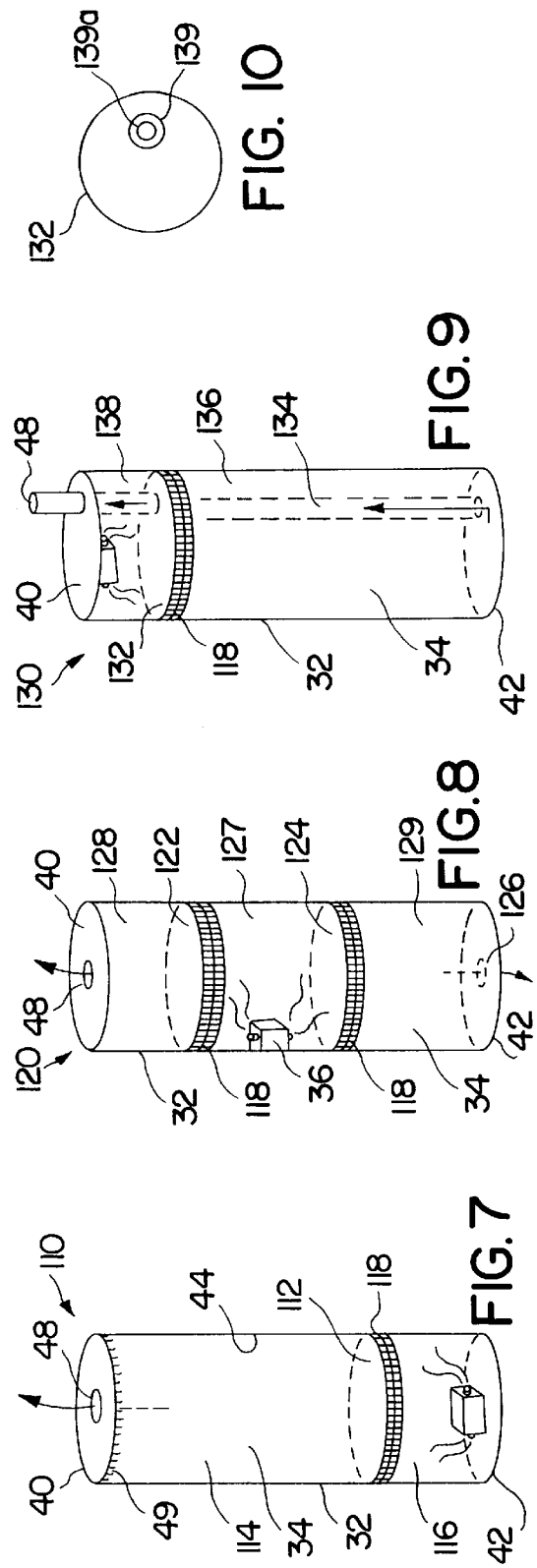

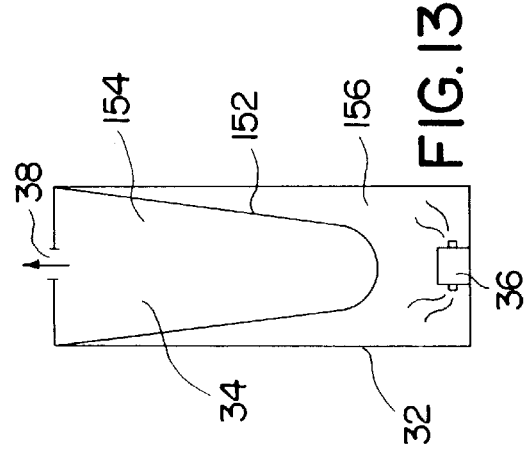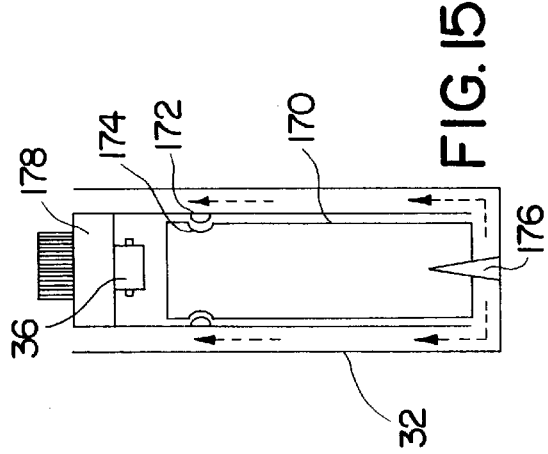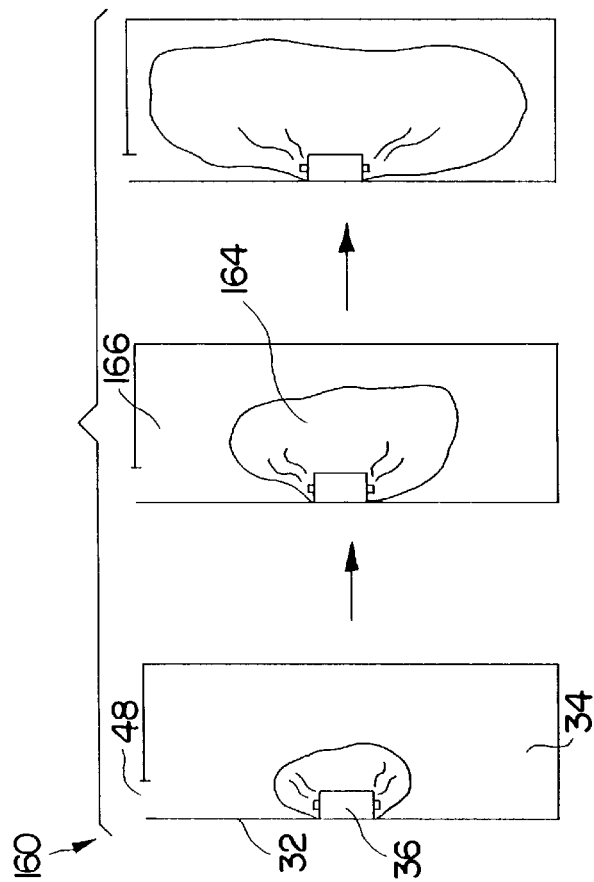

DEVICE AND METHOD FOR DELIVERING FLUID

This is a continuation-in-part of U.S. application Ser. No. 08/804,286 filed Mar. 3, 1997 now abandoned.

BACKGROUND OF THE INVENTION

1. Field of the Invention

The present invention relates in general to fluid delivery systems and, more particularly, to a device and method for controllably delivering fluid from a housing to the surrounding environment.

2. Background of the Invention

Devices for delivering fluid from a container have been know in the art for many years. In particular, many of these devices make use of wick based systems. In these systems, one end of a wick is typically placed in the fluid to be delivered, while the other end is either exposed to or in contact with the surrounding environment. These devices make use of capillary action to transport the fluid through the wick for delivery.

While wick and capillary based devices work well in certain applications, these devices lose their effectiveness when the fluid is required to travel too far against gravity. Moreover, because these devices rely on capillary action, it often takes an unacceptable amount of time to deliver the fluid.

Still other devices make use of gravity based systems. These systems typically rely on the force of gravity to deliver fluid from a container. Although these gravity based devices have worked well, they are unable to deliver fluid to points above the fluid level. Moreover, because these devices rely on the force of gravity, they are often incapable of delivering fluid at a rate necessary for certain applications.

SUMMARY OF THE INVENTION

The present invention comprises a device for delivering a fluid from a housing to the surrounding environment against the force of gravity. The fluid delivery device comprises a housing, a fluid contained within the housing, and a gas generating pump. The housing further consists of an interior region, an inner surface, and an opening positioned above at least a portion of the fluid. In a preferred embodiment, the opening is associated with a channel or conduit, to facilitate the flow of fluid toward the opening. The fluid may comprise any liquid, gelatinous material, or even certain gases. Similarly, the gas generating pump may comprise any conventional gas releasing electrochemical cell, or any other device which is capable of releasing gas into a contained area.

Upon activation of the gas generating pump, gas forces the fluid through the channel or conduit, against gravity and out of the opening. In a preferred embodiment, the opening is further associated with a means for controllably releasing the fluid from the housing. Such controlled release means may consist of one or more porous plugs or an emanator pad, through which the fluid may diffuse to enter the surrounding environment as a vapor or a liquid, or an adjustable valve, which may be used to control the fluid flow out of the housing. Moreover, the association of a decorative element with the opening or a controlled release means is likewise contemplated.

In another preferred embodiment, the fluid delivery device further comprises a moveable member, impermeable to the fluid contained within the housing, separating the fluid from the gas generating pump. The moveable member, preferably comprising one or more piston members, a flexible bladder, or an expandable bladder, acts in combination with the inner surface of the housing to create both a compressible reservoir filled with the fluid and an expandable chamber in communication with the gas generating pump. Upon activation of the gas generating pump, gases fill the expandable chamber which, in turn, expands. As result, the moveable member forces the fluid in the compressible reservoir to exit the housing out of the opening.

BRIEF DESCRIPTION OF THE DRAWINGS

FIG. 1 of the drawings is a side elevational view of a fluid delivery device according to one embodiment of the present invention;

FIG. 2 of the drawings is a perspective view of a fluid delivery device according to another embodiment of the invention;

FIG. 3 of the drawings is a side elevational view of a fluid delivery device according to yet another embodiment of the invention;

FIG. 4 of the drawings is a cross sectional view of FIG. 3, taken along the lines 4—4;

FIG. 5 of the drawings is a perspective view of the device according to FIG. 3;

FIGS. 6a–6e of the drawings are side elevational views of a fluid delivery device having a controlled release means;

FIG. 7 of the drawings is a perspective view of a fluid delivery device having a piston member;

FIG. 8 of the drawings is a perspective view of a fluid delivery device having two piston members;

FIG. 9 of the drawings is a perspective view of a fluid delivery device having a piston member in combination with a conduit;

FIG. 10 of the drawings is a top plan view of the piston of FIG. 9;

FIG. 11 of the drawings is a side elevational view of a fluid delivery device having a piston member and a channel;

FIG. 12 of the drawings is a top plan view of the piston of FIG. 11;

FIG. 13 of the drawings is a side elevational view of a fluid delivery device having a flexible bladder;

FIG. 14 of the drawings is a side elevational view of a sequence showing a fluid delivery device with an expandable bladder; and FIG. 15 of the drawings is a side elevational view of a fluid delivery device having a replaceable cartridge.

DETAILED DESCRIPTION OF THE INVENTION

While this invention is susceptible of embodiment in many different forms, there is shown in the drawings and will hereinafter be described in detail, several specific embodiments with the understanding that the present disclosure is to be considered as an exemplification of the principles of the invention and is not intended to limit the invention to the embodiments so illustrated.

Fluid delivery device 30 is shown in FIG. 1 as comprising housing 32, fluid 34, and gas generating pump 36. Although housing 32 is preferably constructed of a plastic or polymeric material, it is likewise contemplated that the housing may be constructed of any conventional material used for housing fluids. Moreover, although fluid delivery device 30 is pictured as being substantially cylindrical in shape, it is contemplated that the device may take any desired shape including, but not limited to substantially rectangular, substantially triangular, substantially spherical, substantially arbitrary, etc.

Housing 32 consists of top end 40, bottom end 42, inner surface 44, interior region 46, and at least one opening 48. Opening 48 is preferably positioned above at least a portion of fluid 34, which is contained in interior region 46 of the housing. Accordingly, as will be discussed in more detail below, fluid 34 must be forced against gravity to flow out of interior region 46 of the housing and through opening 48. Moreover, although only one opening is shown in FIG. 1, it is contemplated that the fluid delivery device consist of multiple openings. In addition to the number of openings, the size of the openings may also be varied to, for instance, vary the rate of fluid delivery.

Opening 48 is preferably associated with and in fluidic communication with a channel 50 for facilitating the flow of fluid 34 out of fluid reservoir 54 and to the opening. The arrows show the direction of fluid flow. Specifically, the use of channel 50 allows placement of gas generating pump 36 inside of interior region 36 of the housing, or in communication with the interior region. In effect, the channel acts as a barrier between the fluid reservoir 54 and the conduit in which fluid 34 may flow against the force of gravity to reach opening 48. Furthermore, a fluid tight seal 49 preferably covers opening 48 before use. Seal may comprise any material, such as a plastic film, metallized plastic film, aluminum foil, or other equivalent film like materials, that is impermeable to both fluid 34 and the ambient surroundings. The seal maintains the fluid within the device, to prevent its spillage or premature evaporation. Fluid 34 may comprise any liquid, gelatinous material, or gas with a density higher than the density of the gas emitted from the gas generating pump. Specifically, the fluid may be chosen from at least one of the group including, but not limited to, perfumes, aromatic solvents, oils, pesticides, insect repellents, air fragrances, medicines, or combinations thereof.

Gas generating pump 36 preferably comprises a conventional gas releasing electrochemical cell, such as those disclosed in U.S. Pat. Nos. 5,427,870 and 5,454,922 to Joshi et al., both of which are incorporated herein by reference. Moreover, other electrochemical cells capable of generating gases such as oxygen, hydrogen, nitrogen, halogens (e.g. $Cl_2$, bromine, iodine), carbon dioxide, and mixtures thereof are also known and contemplated. (See e.g., U.S. Pat. Nos. 4,402,817 and 4,522,698 to Maget (Jun. 11, 1985) which describe electrochemical cells.) Preferred electrochemical cells for use with the invention include metal electrolyte electrochemical cells capable of generating hydrogen or oxygen. Electrochemical cells include solid polymer electrolyte-based oxygen or hydrogen generators, zinc-air type hydrogen gas generating batteries (see, e.g., U.S. Pat. No. 5,245,565 to Winsel (Sep. 7, 1993) or U.S. Pat. No. 4,023,648 to Orlitzky et al.), $Cu(OH)_2$ or carbonate-based oxygen generating cells, NaSiCON-based $CO_2/O_2$ generating cells (see, International Application No. PCT/US96/04359 (International Publication No. WO 96/30563, published Oct. 3, 1996) to Ceramatec, Inc. (corresponding to co-owned, copending U.S. patent application Ser. No. 08/413,635 filed on Mar. 30, 1995, now U.S. Pat. No. 5,593,552), or nitrogen generating batteries (see, e.g., U.S. Pat. No. 5,427,870 (Jun. 27, 1995). The contents of all of these referenced patents and patent applications are incorporated herein by reference. Notably, some cells require separate power sources (e.g. a battery), while others are self-powered.

In operation, gas generating pump 36 is positioned within device 30 such that gases generated therefrom are emitted into interior region 46 of housing 32. Although the gas generating pump is preferably associated with top end 40 of the housing, it is likewise contemplated that gas generating pump 36 need only be positioned in communication with interior region 46 of the housing. Moreover, while the term gas generating pump is used in the present disclosure, it will be understood for the purposes of this invention that the term gas generating pump may include any device which either releases a gas into a contained region or increases pressure in one closed region as compared to another closed region. Preferably, the gas generating pump is activated by conventional means, such as a switch or lever, that is accessible from outside of the housing.

Specifically, once seal 49 is removed and gas generating pump 36 is actuated, gases emitted from the gas generating pump increase the pressure on surface 35 of fluid 34 contained within housing 32. This increase in pressure, in turn, forces fluid 34 through channel 50 and to a release point—namely opening 48 which is in communication with either the surrounding environment or a controlled release means (discussed below). Greater pressure on surface 35 of the liquid as compared to that at the release point forces the fluid to flow toward the position of lower pressure, namely opening 48. Of course, inasmuch as gravity works against the fluid, which must flow upward toward opening 48, it will be readily understood by those of ordinary skill in the art with the present disclosure before them that the pressure applied to the surface of the fluid by gas generating pump 36 will compensate for and overcome the force of gravity.

In another embodiment, shown in FIG. 2, the channel of FIG. 1 is replaced by conduit 58, which is associated with opening 48 and in communication with fluid 34. (Inasmuch as fluid delivery device components are substantially similar, like reference numerals will be used to designate similar components throughout this application.) As with the use of channel 50 in FIG. 1, downward pressure on fluid surface 35 from gas generating pump 36 forces fluid 34 up through conduit 58 toward opening 48, where it is released in any desired manner.

In yet another alternative to the channel of FIG. 1, and as is depicted in FIGS. 3–5, fluid delivery device 60 comprises housing 32, fluid 34, gas generating pump 36, and outer shell 62. Outer shell 62 is attached to the outer surface of housing 32 such that fluid passageways 64 are formed between the housing and the outer shell. Preferably, housing is closed at top end 40, and open at bottom end 42, so that fluid 34 contained within housing 32 may freely exit the bottom end of the housing. Moreover, as can be seen, the bottom end of shell 62 preferably extends below the bottom end of housing 32 to facilitate free flow of the fluid.

Upon activation of gas generating cell 36, fluid 34 is forced downward through housing 32, out bottom end 42, and upward through fluid passageways 64. From here, the fluid exits the device, to either the surrounding environment or a controlled release means (described below).

In another series of embodiments, opening 48 in housing 32 may be associated with and in fluidic communication with a means for controllably releasing fluid 34 into the surrounding environment. In one embodiment, shown in FIG. 6a, opening 48 is associated with a controlled release means taking the form of porous plug 70, which has both a top surface 72 and bottom surface 74. Although porous plug 70 preferably comprises a microporous polymer membrane, the plug may be fabricated from other materials including, but not limited to porous plastic, porous polymers, porous ceramics, porous metals, porous glass, fibrous materials, cellulose, cellulose derivatives, or any combinations thereof. Moreover, although porous plug 70 is preferably positioned in opening 48 by an interference fit, the porous plug may also be held in place by other conventional means such as adhesive, shoulders, fingers or the like situated within channel 50. Once positioned, top surface 72 of the porous plug is preferably exposed to the surrounding environment.

In operation, fluid 34 is forced toward opening 48 by gas generating pump 36, before it comes into contact with bottom surface 74 of porous plug 70. At this point, the pressure exerted on fluid 34 forces the fluid to diffuse through the porous plug until it reaches top surface 72. From here, the fluid may volatilize into the surrounding environment as a vapor, or be released upon contact with the porous plug as a liquid. In particular, factors such as the rate of release of gas from the gas generating pump, properties of the particular fluid used (density, viscosity, surface tension, etc.), and properties of the porous plug (plug material, pore size, etc.) control the rate of release of fluid from the device. Preferably, a linear, constant, and/or uniform release rate is obtained with the use of porous plug 70.

In another embodiment, illustrated in FIG. 6b, the controlled release means comprises the combination of first porous plug 80, having top surface 82 and bottom surface 84, second porous plug 86, also having top surface 88 and bottom surface 89, and air gap 85 positioned therebetween. Like the porous plug of FIG. 6a, both first 80 and second 86 porous plugs are positioned in opening 48 by an interference fit and are preferably constructed from a polymeric membrane. However, the plugs need not be constructed of the same material, nor have the same diffusive properties.

In operation, fluid 34 is forced through channel 50 and into contact with bottom surface 84 of first porous plug 80. The fluid then diffuses through the first plug, before entering air gap 85 in a substantially vapor form. The vapor then enters bottom surface 89 of second porous plug 86 and diffuses through the second plug, before volatilizing from top surface 88 into the surrounding environment. It is contemplated that at least a portion of the vapor phase entering the second porous plus is converted back into its liquid phase before volatilizing from the top of the second porous plug. Of course, it is also contemplated that fluid 34 may enter the surrounding environment in a liquid phase, for instance, by contact of an object with the second porous plug. The use of two porous plugs preferably controls and linearizes the rate of release of the fluid 34 into the surrounding environment.

In yet another embodiment, shown in FIG. 6c, the controlled release means comprises emanator pad 90, which may be constructed of any porous medium. Although emanator pad 90 may be proximately associated with opening 48, it is likewise contemplated that the emanator pad is associated with a decorative element, such as artificial flower 92. Indeed, other decorative elements, including but not limited to artificial leafs, decorative bottles, figurines, children's toys, and animal figurines, are also contemplated for use. For example, an artificial flower may give off a pleasant aroma or an artificial bug may release an insect repellant. Additionally, these decorative elements may be placed in fluid communication with opening 48 through conduit means, such as conduit 94. Of course, although discussed in reference to emanator pad 90, decorative elements may be used in combination with any of the other disclosed controlled release means.

In operation, emanator pad 90 absorbs or adsorbs fluid 34 forced through opening 48 by gas generating pump 36. Fluid 34 travels through emanator pad 90 to emanator pad surface 96 by forced diffusion. From here, the fluid either volatilizes into the surrounding environment as a vapor, or is applied to an emanator pad surface-contacting object. To this end, and is seen in FIG. 6d, the emanator pad may function as an applicator pad 98, from which fluid 34 may be applied to an object contacting the applicator pad. Furthermore, it is also contemplated that the size and/or surface area of the emanator pad may be increased to, for instance, increase the release rate of fluid 34 into the surrounding environment. In still another embodiment, depicted in FIG. 6e, controlled release means comprises valve 100. While valve 100 may consist of a one-way valve to decrease the flow of fluid 34 through opening 48 or channel 50, the valve may also consist of an adjustable valve for regulating fluid flow from housing 32 and out of opening 48.

Of course, it is readily contemplated that these controlled release means embodiments, namely those shown in FIGS. 6a–6e, may be used in combination to achieve a desired fluid release rate, or a desired fluid release phase (ie liquid or vapor). For instance, an adjustable valve may be used in combination with a porous plug, an emanator pad, and/or a decorative element. Moreover, any of these controlled release means may be combined with the different embodiments of the fluid delivery device described herein.

In another preferred embodiment, shown in FIG. 7, fluid delivery device 110 comprises housing 32, fluid 34, gas generating pump 36, and a moveable member, shown here as piston 112. Together, piston 112, inner surface 44 of the housing, and top end 40 of the housing define a compressible reservoir 114, at least partially filled with fluid 34. Opening 48 is preferably in fluidic communication with the compressible reservoir. Moreover, piston 112, inner surface 44, and bottom end 42 of the housing define an expandable chamber 116. Gas generating pump 36 is positioned such that it is in communication with the expandable chamber, preferably attached to the bottom inner surface of the housing. Notably, compressible reservoir 114 is fluidically isolated from expandable chamber 116.

As can be seen, piston 112 substantially corresponds to the shape of the inner periphery of housing 32. Although piston 112 is shown in FIG. 7 as having a substantially circular shape to correspond to the substantially cylindrical housing, the piston may be constructed to match any housing dimensions. Moreover, piston 112 may be of any desired thickness, depending on the application, as would be readily contemplated by those of ordinary skill in the art with the present disclosure before them.

Additionally, an appropriately sized sealing ring 118 may be associated with a groove or an indentation in piston 112. When the piston is positioned inside housing 32, sealing ring 118, consisting of rubber, latex, or any other conventional fluid tight sealing materials, is positioned between piston 112 and inner surface 44 of the housing. Accordingly, the sealing ring assists in forming a fluid tight seal to preserve fluidic isolation between compressible reservoir 114 and expandable chamber 116, while still allowing the piston to slide freely within the housing. Although sealing ring 118 is preferred, compressible reservoir 114 may be fluidically isolated from expandable chamber 116 by other means, such as constructing the outer periphery of the piston with a rubber or other fluid tight material.

In operation, after breaking seal 49 to expose opening 48 to the surrounding environment (or a controlled release means), gas from gas generating pump 36 fills expandable chamber 116. When the pressure created inside expandable chamber 116 placed on piston 112 becomes great enough to overcome the weight of fluid 34 in compressible reservoir 114, the force of gravity, and any friction created between sealing ring 118 and inner surface 44 of the housing, the piston moves upward and away from the bottom end of the housing. Inasmuch as the opening is exposed to an adjacent element, namely the surrounding environment or a selected controlled release means, piston 112 forces fluid 34 through opening 48 and into the adjacent element. Accordingly, the compressible reservoir contracts upon upward movement of the piston and loss of fluid, while the expandable chamber expands with the addition of gas. The piston will continue to force fluid out of the housing until no fluid remains in the compressible reservoir.

In yet another embodiment shown in FIG. 8, fluid delivery device 120 comprises housing 32, fluid 34, gas generating pump 36, and multiple moveable members (here first piston 122 and second piston 124). In addition to opening 48 in top end 40, housing 32 also comprises another opening 126 in bottom end 42. First piston 122, second piston 124, and inner surface 44 of the housing define an expandable chamber 127, while the first and second pistons and the respective top and bottom ends of the housing define first and second compressible reservoirs, 128 and 129 respectively. Although gas generating pump is preferably attached to inner surface 44 of the housing within expandable chamber 127, it is likewise contemplated that the gas pump need only be placed in communication with the expandable chamber. Moreover, like the piston of FIG. 7, first and second pistons 122 and 124 are each preferably associated with a sealing ring 118 to fluidically isolate expandable chamber 127 from first and second compressible reservoirs 128 and 129.

Much like the fluid delivery device of FIG. 7, upon activation of gas generating pump 36, gas emitted from the gas generating pump fills expandable chamber 127, until the pressure forces one or both of first and second pistons 122 and 124 to move toward the corresponding openings 48 and 126, respectively, in top 40 and bottom 42 ends of the housing. The pistons, in turn, force fluid 34 out of the openings, and either into the surrounding environment or to a controlled release means. Although the first and second pistons preferably move along the inner surface of the housing at a substantially equivalent rate, it is contemplated that the pistons may slide at different rates, thus forcing the fluid out of the top and bottom openings at different rates (for example, the force of gravity may increase the rate of downward movement of the second piston as compared to the rate of upward movement of the first piston). In still another embodiment, illustrated in FIG. 9, fluid delivery device 130 comprises housing 32, fluid 34, gas generating pump 36, opening 48, and moveable member, again a piston 132. Opening 48 is further associated with a conduit 134, which extends into fluid communication with a compressible reservoir 136, defined by piston 132, inner surface 44 of the housing, and bottom end 42 of the housing. Gas generating pump 36 is positioned such that it is in communication with expandable chamber 138, which is defined by piston 132 and top end 40 of the housing.

Like the pistons of the above described embodiments, piston 132 is also associated with a sealing member 118 such as an O-ring to maintain fluidic isolation between compressible reservoir 136 and expandable chamber 138. However, inasmuch as conduit 138 extends from opening 38 to compressible reservoir 136, piston 132 further consists of a hole 139 substantially matching the outer peripheral dimensions of the conduit, also shown in FIG. 10. Accordingly, to maintain the fluidic isolation between the compressible reservoir and the expandable chamber, hole 139 is preferably associated with a sealing member 139a, such as a rubber O-ring, which allows piston 132 to slide along the length of conduit 134, but which also provides a fluid tight seal.

In operation, gas from gas generating pump 36 fills expandable chamber 138 and forces piston 132 downward. This downward piston motion, in turn, forces fluid 34 up through conduit 134, and through opening 48. The piston continues downward until it reaches the bottom of housing 32, at which point substantially all of the fluid is forced out of the interior region of the housing.

In an alternative fluid delivery device 140, shown in FIGS. 11 and 12, opening 48 is associated with a channel 142 which replaces the conduit of FIG. 9. Accordingly, instead of a hole in the piston through which the conduit extends, piston 144 is configured so as to match the shape of the inner periphery of the housing—specifically, the inner periphery of the housing excluding the channel. This configuration allows the forced downward movement of piston 144 to force fluid 34 up through channel 142 and out through opening 48.

In another embodiment, illustrated in FIG. 13, fluid delivery device 150 comprises housing 32, fluid 34, gas generating pump 36, opening 48, and a moveable member, here a flexible bladder 152. Flexible bladder 152 may be constructed of a rubber, latex, or other fluid impermeable material. Moreover, although flexible bladder 152 is preferably attached to the open end of the housing, the bladder may also be sealably attached to inner surface 44 of housing 32. Inasmuch as flexible bladder 152 defines a compressible reservoir 154 on one side, and an expandable chamber 156 on the other, the attachment points are preferably fluid tight so as to maintain fluidic isolation therebetween. Fluid 34 is housed in compressible reservoir 154, while gas generating pump is in communication with expandable chamber 156.

Upon activation of gas generating pump 36, gas fills expandable chamber 156, thus placing pressure on flexible bladder 152. This pressure, in turn, forces the flexible bladder, and thus the compressible chamber, to contract. Accordingly, fluid 34 is forced out of opening 48. Of course, the opening is preferably associated with a controlled release means (not shown), such as a decorative element and an emanator pad, to facilitate delivery of the fluid.

In yet another embodiment, shown in FIG. 14, fluid delivery device 160 comprises housing 32, fluid 34, gas generating pump 36, opening 48, and a moveable member, here an expandable bladder 162. Expandable bladder 162 may be constructed of any material that is both expandable and impermeable to the fluid contained within the housing, for instance latex or rubber. However, other conventional expandable materials are likewise contemplated as would be understood by those with ordinary skill in the art with the present disclosure before them. Furthermore, gas generating pump 36 is positioned in communication within an expandable chamber 164, which is defined by the inside of expandable bladder 162. Fluid 34 is contained in compressible reservoir 166, which is defined by the expandable bladder and inner surface 44 of housing 32.

As can be seen, once gas generating pump 36 begins emitting gas into expandable chamber 164, pressure is placed on expandable bladder 162. This pressure causes the bladder to expand, much like a balloon, into the interior region of the housing. This expansion, in turn, forces fluid 34 out of opening 48, and to the surrounding environment or a controlled release means. The bladder expands until the housing prevents further expansion, preferably until substantially all of the fluid is forced out of the housing. Again, the fluid may be released directly out of the housing, or, onto/into a porous plug or emanator pad where the fluid can then volatize into a vapor in the ambient environment.

As shown in FIG. 15, fluid 34 may be contained within a replaceable and disposable cartridge 170. Such a cartridge may, for example, be held in the housing by a removable cap, or locked into the housing by a snap-fit fastening mechanism such as ridge 172 and groove 174. Cartridge 170 may be constructed from a relatively rigid material, such as a hard plastic or metal, or may be relatively pliable and flexible, such as a plastic bag.

Moreover, cartridge 170 further consists of a means to cooperate with housing 32 during use of the device, to, in turn, allow fluid 34 to be released from the cartridge. One such cooperation means comprises spike 176, or other conventional means capable of puncturing the bottom of cartridge 170, to allow the fluid to escape from the cartridge. To this end, a seal, or any material that is easily penetrated, is contemplated for placement over the bottom of the cartridge to prevent escape of the fluid before use. Another cooperation means consists of the top of cartridge 170 being removable, as for instance with the use of a conventional removable seal. Moreover, the top may also be puncturable, as for instance by a knife, pen, similar readily available object, or even spikes/puncturing means attached to a cap 178 positioned to seal the top of housing 32. A removable or puncturable top would allow cooperation of the fluid with gas generating pump 36. Of course, one of ordinary skill in the art will understand that numerous other mechanisms for facilitating cooperation between the replaceable cartridge and the housing are likewise contemplated. Cartridge 170 may be removed and replaced after the fluid has been released. A replaceable cartridge may used in combination with any number of the abovedescribed embodiments.

The foregoing description and drawings are merely to explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A device for delivering fluid comprising:
   a housing having a top end, an interior region, an interior surface, and one or more openings;
   a fluid contained within at least a portion of the interior region of the housing, wherein at least a portion of the fluid is positioned below at least one of the one or more openings; and
   means for controllably forcing the fluid through the at least one opening in the housing, wherein the controlled forcing means comprises a gas generating pump, which, in turn, forces the fluid through the at least one opening.

2. The device according to claim 1 wherein the device further comprises the at least one opening being associated with a channel through which the fluid flows to reach the opening.

3. The device according to claim 1 wherein the at least one opening in the housing is associated with and in fluidic communication with a means for controllably releasing the fluid into the surrounding environment.

4. The device according to claim 3 wherein the controlled release means comprises at least one of a porous plug or an emanator pad.

5. The device according to claim 4 wherein the at least one of the porous plug or emanator pad is associated with at least one decorative element from the group consisting of artificial flowers, artificial leafs, decorative bottles, figurines, children's toys, and animal figurines.

6. The device according to claim 4 wherein the porous plug is selected from at least one of the group consisting of porous plastic, porous polymers, porous ceramics, porous metals, porous glass, fibrous material, cellulose or cellulose derivatives.

7. The device according to claim 3 wherein the controlled release means comprises an adjustable valve for controlling fluid flow.

8. The device according to claim 3 wherein the controlled release means comprises:
   a first porous plug having a top surface and a bottom surface;
   a second porous plug having a bottom end and a top end wherein the top end is in at least partial contact with the fluid and the bottom end is facing the top surface of the first porous plug; and
   a gap between the top surface of the first porous plug and the bottom end of the second porous plug.

9. The device according to claim 1 wherein the controlled forcing means includes at least one moveable member separating the fluid from the gas generating pump, wherein the moveable member is substantially impermeable to the fluid.

10. The device according to claim 9 further including:
    the at least one moveable member operatively associated with and movable within the interior region of the housing;
    a compressible reservoir at least partially filled with the fluid, the compressible reservoir defined by the moveable member and the interior surface of the housing;
    an expandable chamber fluidically isolated from the compressible reservoir; and
    the gas generating pump operatively associated with and in communication with the expandable chamber.

11. The device according to claim 10 wherein the moveable member consists of one of the following from the group of an expandable bladder, a flexible bladder, and a piston-like member.

12. The device according to claim 11 wherein the piston-like member is slidably associated with the interior surface of the housing.

13. The device according to claim 9 further including:
    a fluid conduit having first and second ends;
    the first end of the fluid conduit positioned in fluid communication with the fluid contained in the housing; and
    the second end of the fluid conduit positioned in communication with the at least one opening in the housing.

14. The device according to claim 1 further comprising means for resupplying additional fluid into the interior region of the housing.

15. The device according to claim 14 wherein the resupply means comprises a replaceable fluid cartridge.

16. The device according to claim 1 wherein at least one opening is positioned in the top of end of the housing.

17. A method for controllably delivering fluid, the method comprising:
    placing a fluid in a housing having an interior region and one or more openings such that at least a portion of the fluid is positioned below at least one of the one or more openings;

positioning a gas generating pump in communication with the fluid; and actuating the gas generating pump such that the fluid is forced through the at least one opening in the housing.

18. A device for delivering fluid comprising:

a housing having a top end, an interior region, an interior surface, and one or more openings;

a fluid contained within at least a portion of the interior region of the housing, wherein at least a portion of the fluid is positioned below at least one of the one or more openings; and means for controllably forcing the fluid through the at least one opening in the housing, wherein the controlled forcing means comprises a gas generating pump;

the at least one opening in the housing is associated with and in fluidic communication with a means for controllably releasing the fluid into the surrounding environment, the controlled release means comprising at least one of a porous plug or an emanator pad.

19. A device for delivering fluid comprising:

a housing having a top end, an interior region, an interior surface, and one or more openings;

a fluid contained within at least a portion of the interior region of the housing, wherein at least a portion of the fluid is positioned below at least one of the one or more openings; and means for controllably forcing the fluid through the at least one opening in the housing, wherein the controlled forcing means comprises a gas generating pump and includes at least one moveable member separating the fluid from the gas generating pump, wherein the moveable member is substantially impermeable to the fluid.

20. A device for delivering fluid comprising:

a housing having a top end, an interior region, an interior surface, and one or more openings;

a fluid contained within at least a portion of the interior region of the housing, wherein at least a portion of the fluid is positioned below at least one of the one or more openings;

means for controllably forcing the fluid through the at least one opening in the housing, wherein the controlled forcing means comprises a gas generating pump; and means for resupplying additional fluid into the interior region of the housing, wherein the resupply means comprises a replaceable fluid cartridge.

* * * * *